United States Patent [19]

Shiba et al.

[11] Patent Number: 5,034,510
[45] Date of Patent: Jul. 23, 1991

[54] ANTIBACTERIAL SUBSTANCE

[75] Inventors: Tetsuo Shiba, Toyonaka; Tatsuhiko Hongu, Yokohama; Yuji Tokushige, Tokyo, all of Japan

[73] Assignee: Shin-Etsu Chemical Co., Ltd., Tokyo, Japan

[21] Appl. No.: 432,411

[22] Filed: Nov. 6, 1989

Related U.S. Application Data

[63] Continuation of Ser. No. 90,600, Aug. 28, 1987, abandoned.

[30] Foreign Application Priority Data

Aug. 29, 1986 [JP] Japan ............... 61-202815

[51] Int. Cl.$^5$ ............... C07K 7/08; C07K 7/10
[52] U.S. Cl. ............... 530/326; 530/324; 530/325
[58] Field of Search ............... 530/326, 325, 324

[56] References Cited

U.S. PATENT DOCUMENTS 3,720,690  3/1973  King et al. ............... 548/525
4,350,627  9/1982  Castiglione et al. ............... 530/328

OTHER PUBLICATIONS

Merrifield et al., Biol. Abstr. 76(10)–70382 (11/3/83).
Shiba et al., Chem. Abstr. vol. 101, No. 53121a (1984).
Andreu et al., Chem. Abstr. vol. 103, No. 123890t (1985).
Van Hopstem et al., Biol. Abstr. 80(4): 32029 (8/15/85).
Nakai et al., Peptide Chemistry pp. 207–212 (1985).
Shiba et al., Walter de Gruyter & Co., Berlin New York (1987 published).
E. Wunsch: "Synthese von Peptiden," in Houben-Weyl, Methoden der Organischen Chemie, edition 4, vol. XV/1, 1974, pp. 6–7, Georg Thieme Verlag, Stuttgart, DE.

*Primary Examiner*—John Doll
*Assistant Examiner*—Christina Chan
*Attorney, Agent, or Firm*—Foley & Lardner

[57] ABSTRACT

An antibacterial substance comprising a peptide comprising a fragment constituting lepidopteran A and containing the N-terminal amino acid residue of the lepidopteran A, wherein the carboxyl group at the C-terminal of said peptide is substituted with an alkyl amide group represented by Formula (I):

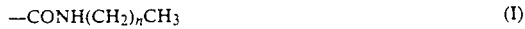

$$-\text{CONH}(\text{CH}_2)_n\text{CH}_3 \qquad (\text{I})$$

wherein n is an integer of 2 to 16.

This antibacterial substance shows good antibacterial activities against various bacteria, and is useful as pharmaceuticals and agricultural chemicals.

1 Claim, 1 Drawing Sheet

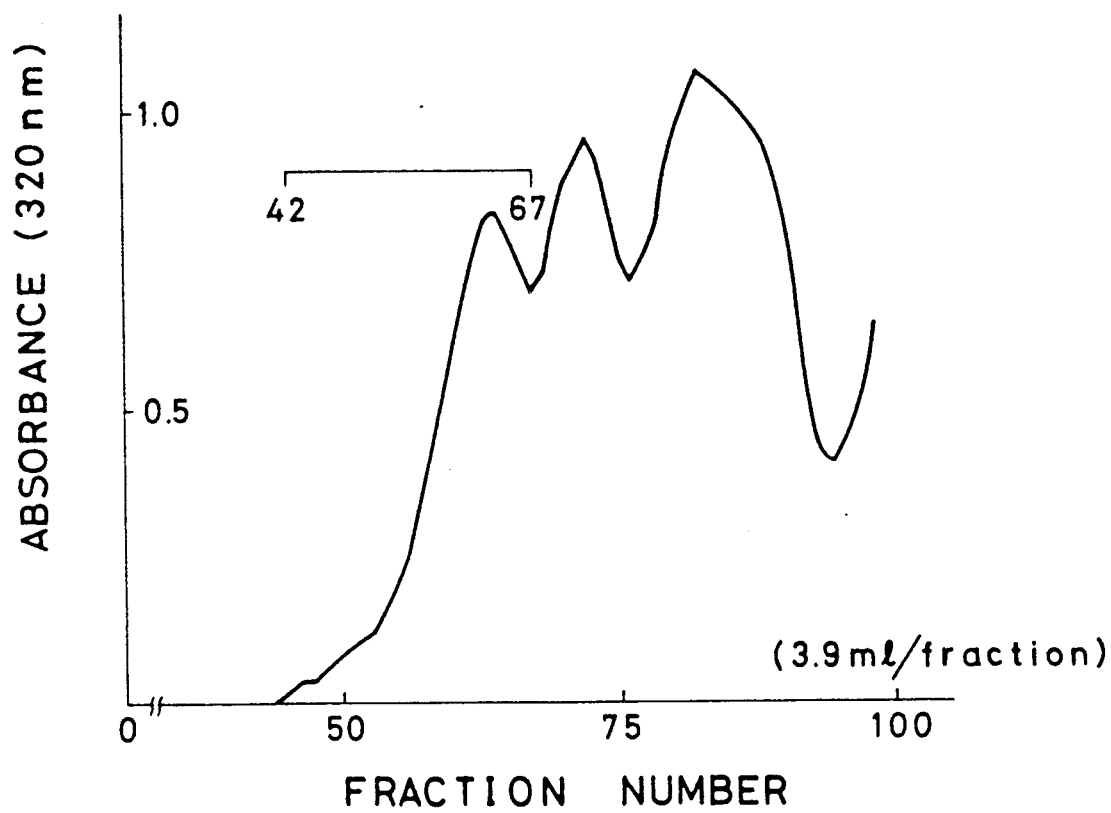

ANTIBACTERIAL SUBSTANCE

This application is a continuation of application Ser. No. 090,600, now abandoned, filed Aug. 28, 1987.

BACKGROUND OF THE INVENTION

1. Field of the Invention

This invention relates to a novel antibacterial substance, and, particularly, to a novel lepidopteran type antibacterial substance having high antibacterial activities.

2. Description of Related Art

An immune response substance lepidopteran is known to be produced by vaccinating silkworm with killed *E. coli* treated with formalin. Lepidopteran includes three homologues called lepidoperan A, B and C, respectively, whose structure has all been made clear, and among which lepidopteran A has been made available through a synthetic route. Synthetic lepidopteran A has substantially the same antibacterial activities with those of the naturally occurring lepidopteran A, but it shows insufficient antibacterial activities as a practical antibacterial agent used in, for example, agricultural chemicals, pharmaceuticals and so forth, and there is necessity for improvement.

SUMMARY OF THE INVENTION

Accordingly, an object of this invention is to provide a novel lepidopteran type antibacterial substance having high antibacterial activities and having wide and high utility as agricultural chemicals, pharmaceuticals, etc.

The present inventors have discovered that a novel lepidopteran type antibacterial substance showing high antibacterial activities can be obtained by introducing an alkyl amide group into the C-terminal of a peptide comprising a fragment constituting lepidopteran.

According to this invention, there is provided an antibacterial substance comprising a peptide comprising a fragment constituting lepidopteran A and containing the N-terminal amino acid residue of the lepidopteran A, wherein the carboxyl group at the C-terminal of said peptide is substituted with an alkyl amide group represented by Formula (I):

$$-CONH(CH_2)_nCH_3 \qquad (I)$$

wherein n is an integer of 2 to 16.

The novel antibacterial substance of this invention has good antibacterial activities. In a particularly preferred embodiment, it can show antibacterial activities several factors of ten greater than lepidopteran A, and can be useful in the development of various new agricultural chemicals, pharmaceuticals, etc.

BRIEF DESCRIPTION OF THE DRAWING

FIG. 1 shows an elution pattern in the gel filtration using Sephadex LH-60, carried out on a product obtained in Experiment 33 described herein.

DETAILED DESCRIPTION OF THE INVENTION

Lepidopteran A has the structure as shown by the following Formula (II):

$$\begin{aligned}
&\overset{1}{\text{H}-\text{Arg}}-\text{Trp}-\text{Lys}-\text{Ile}-\text{Phe}-\overset{6}{\text{Lys}}-\text{Lys}-\text{Ile}- \\
&\text{Glu}-\text{Lys}-\text{Met}-\overset{12}{\text{Gly}}-\text{Arg}-\text{Asn}-\text{Ile}-\text{Arg}-\text{Asp}- \\
&\overset{18}{\text{Gly}}-\text{Ile}-\text{Val}-\text{Lys}-\text{Ala}-\overset{23}{\text{Gly}}-\text{Pro}-\text{Ala}-\text{Ile}- \\
&\text{Glu}-\text{Val}-\text{Leu}-\overset{30}{\text{Gly}}-\text{Ser}-\text{Ala}-\text{Lys}-\text{Ala}-\overset{35}{\text{Ile}}-\text{NH}_2
\end{aligned} \qquad (II)$$

As will be seen from the above Formula (II), lepidopteran A is a polypeptide comprising thirty five (35) amino acid residues, wherein the carboxyl group present at the C-terminal (i.e., the right terminal in Formula (II)) takes the form of an amide to form —CONH$_2$.

In the description hereinbelow, the respective amino acid residues in the amino acid sequence represented by Formula (II) are numbered in the manner that Arg at the N-terminal (the left terminal) is numbered as 1, and subsequent amino acid residues as 2, 3 and so on sequentially in the right direction until they end with 35 at Ile of the C-terminal (the right terminal), and lepidopteran A is abridged as:

$$\text{H}-(1\text{-}35)-\text{NH}_2.$$

Also, a peptide comprising the fragments occurring from the first Arg to No. m amino acid residue of lepidopteran A and having a free amino acid group of the N-terminal and a free carboxyl group at the C-terminal is represented by Formula (III):

$$\text{H}-(1\text{-m})-\text{OH} \qquad (III).$$

For example, the peptide comprising the fragment occurring from 1st Arg to 6th Lys is represented by the formula:

$$\text{H}-(1\text{-}6)-\text{OH}.$$

If a blocking group is attached to the side chain of amino acid residues constituting the peptide represented by Formula (III), such a peptide is represented by the formula:

$$\text{H}-(1\text{-m})_p-\text{OH}$$

and distinguished from the unblocked one by using the subscript p. Also in respect of a peptide in which a blocking group is attached to the amino group at the N-terminal and/or the carboxyl group at the C-terminal, it is represented following the manner of representation for Formula (III).

In the alkyl amide group represented by Formula (I), attached to the C-terminal of the peptide which is the antibacterial substance of this invention, n is an integer of 2 to 16, preferably 3 to 13. It is particularly preferably 7, at which very good antibacterial activities can be obtained.

The peptide, the antibacterial substance of this invention, comprises a fragment constituting lepidopteran A and containing the N-terminal, wherein the number of amino acid residues in said fragment may preferably be 18 or more, particularly preferably 23 or more, in view of the strength of the antibacterial activities obtained.

In a most preferred embodiment of the antibacterial substance of this invention, the number of amino acid residues constituting the above fragment is 23 to 35 and n in Formula (I) is 7.

EXAMPLES

This invention will be described below in detail by Examples. Abbreviations used herein have the following meaning:
DMF: N,N-dimethylformamide
DMSO: Dimethylsulfoxide
NMP: N-methyl-2-pyrrolidone
HMPA: Hexamethylphosphoric acid triamide
THF: Tetrahydrofuran
TFA: Trifluoroacetic acid
TFE: 2,2,2-Trifluoroethanol
ACOH: Acetic acid
AcOEt: Ethyl acetate
Me$_2$S: Dimethylsulfide
EDT: 1,2-Ethanediol
HOBt: 1-Hydroxybenzotriazole
WSCI: 1-Ethyl-3-(3-dimethylaminopropyl)-carbodiimide
DCC: Dicyclohexylcarbodiimide
Boc-: t-Butoxycarbonyl
Tos-: p-Toluenesulfonyl
ClZ-: 2-Chlorobenzyloxycarbonyl
CHO: Formyl
-Bzl: Benzyl
-Pac: Phenacyl
-cHex: Cyclohexyl
-Su: Succinimide
-Np: p-Nitrophenyl
-Pcp: Pentachlorophenyl In the following description, Processes A to F mean the following processes:

Post-Treatment After Condensation

Process A

An instance where a blocked peptide is soluble in ethyl acetate (AcOEt).

A reaction mixture is concentrated under reduced pressure and dissolved in AcOEt. The AcOEt layer is washed in succession with a 10% aqueous solution of citric acid, a saturated aqueous solution of sodium hydrogencarbonate, and saturated brine, and thereafter dried with anhydrous magnesium sulfate. The desiccating agent is filtered out, and the filtrate is concentrated under reduced pressure to obtain a crude product. This crude product is used in subsequent procedures.

Process B

An instance where a blocked peptide is slightly soluble in ethyl acetate or the like.

Saturated brine is added to a reaction mixture containing a blocked peptide. The precipitate formed is collected by filtration and washed in succession with a 10% aqueous solution of citric acid, water, a saturated aqueous solution of sodium hydrogencarbonate, water, methanol (or AcOEt), and ether, and thereafter dried to obtain a crude product. This crude product is used in subsequent procedures.

Post-Treatment of Removal of Boc Group

Process C

Ether is added to a reaction mixture. The precipitate formed is collected by filtration, and sufficiently dried over sodium hydroxide in a desiccator.

Process D

A reaction mixture (a TFA solution) is concentrated to about $\frac{1}{3}$ to $\frac{1}{4}$ under reduced pressure. Thereafter, 10 to 20 ml of 4 to 5N HCl in THF are added thereto and stirred, to which ether is further added. The precipitate formed is collected by filtration, and sufficiently dried over sodium hydroxide in a desiccator.

Post-Treatment of Removal of Phenacyl Group

Process E

Termination of the reaction is confirmed by TLC (thin layer chromatography). After the reaction has been confirmed to have been completed, insolubles are filtered off, and water is added to the filtrate. The precipitate formed is collected by filtration or centrifugal sedimentation, and the precipitate collected is washed with water and further washed with ether to remove acetophenone. The product obtained is dried over phosphorus pentaoxide in a desiccator.

Process F

If the reaction cannot be traced by TLC, acetophenone formed by removal of the phenacyl group is determined by HPLC (high pressure liquid chromatography) (Cosmosil 5C$_{18}$, 4 mm $\phi \times 125$ mm, 30% CH$_3$CN/H$_2$O, 1 ml/min, 240 nm) to confirm the termination of the reaction. After the reaction has been confirmed to have been terminated, treatment is carried out in the same manner as in Process E.

Process for Analysis of Amino Acid of Blocked Peptide

A blocked peptide (0.1 to 1 mg) is put in a pyrex test tube and dissolved by adding TFA (100 μl), to which conc. hydrochloric acid (200 μl) is added to control the ratio of TFA to conc. hydrochloric acid to 1:2 v/v, and the tube is sealed under reduced pressure, followed by hydrolysis under the conditions of 166° C. for 25 minutes (Condition I) or 166° C. for 50 minutes (Condition II). After the tube is opened, the reaction mixture is heated to 60° C. and dried under reduced pressure. The residue obtained is dissolved in a buffering solution of 0.2M citric acid to make a sample for the analysis of amino acids. Trp is perfectly decomposed under the above hydrolytic condition, and the recovery of Ser and Met is lowered. (Recovery of Ser is 0 to 50% and recovery of Met is 30 to 90%, which are greatly affected depending on the hydrolysis time.) Also, since racemization may take place in respect of Ile, a value obtained by adding the value for Ile and the value for allo-Ile is used as the value for Ile.

I. Preparation of Boc-(1–18)$_p$—OH (Experiments 1–34)

In Experiments described below, the antibacterial substance of this invention was prepared according to the following procedures:

First, a straight chain polypeptide comprising eighteen (18) amino acids (which is the same amino acid sequence with the amino acid sequence comprising 18 amino acids at the side of the N-terminal of lepidopteran A), wherein the amino acid at the N-terminal is blocked with Boc (t-butoxycarbonyl) and a free COOH group is present at the C-terminal, is synthesized (Experiments 1 to 34). Hereinafter, this substance is abridged as Boc—(-1-18)$_p$—OH. Next, according to a dehydration condensation of —COOH at the C-terminal of this polypeptide with $CH_3(CH_2)_nNH_2$ (wherein n is an integer of 1 to 17), —COOH at the C-terminal is converted into various types of —$CONH(CH_2)_nCH_3$. Also, the Boc group at the N-terminal is removed with use of TFA to convert it into the $NH_2$-terminal, the blocking group at the side chain other than the —CHO group is cleaved with use of anisole and HF, and then the —CHO group is cleaved with use of $HSCH_2CH_2SH$ and HF. (Experiments 35 to 42)

EXPERIMENT 1

Preparation of Boc-Phe-Lys(ClZ)-OPac (1)

HCl.H-Lys(ClZ)-OPac (14.1 g, 30 mmol) and Boc-Phe-OSu (10.9 mg, 30 mmol) were suspended in 140 ml of DMF, and triethylamine (2.21 ml, 15.7 mmol) was added under ice cooling, followed by stirring. After 30 minutes, triethylamine (1 ml, 7.12 mmol) was added. After further 1 hour, triethylamine (1 ml, 7.12 mmol) was added, followed by stirring overnight at room temperature. N-(2-aminoethyl)-piperazine (0.79 ml, 6 mmol) was added, followed by stirring under ice cooling for 30 minutes. The resulting reaction mixture was subjected to treatment by Process A, and a crude product obtained was recrystallized from a mixed solvent of methanol/AcOEt/hexane. Yield, 16.9 g (82.6%).

Characteristics of the product: m.p., 140° to 142° C.; $[\alpha]_D^{16.5}$ −8.7° C. (c 1.07, DMF).

Elementary analysis: Found: C, 63.43; H, 6.20; N, 6.18; Cl, 5.26%. Calculated as $C_{36}H_{42}N_3O_8Cl$: C, 63.57; H, 6.22; N, 6.18; Cl, 5.21%.

EXPERIMENT 2

Preparation of HCl.H-Phe-Lys(ClZ)-OPac (2)

Boc-Phe-Lys(ClZ)-OPac (1) (14.0 g, 20.6 mmol) obtained in Experiment 1 was dissolved in 400 ml of 1N HCl in AcOH, and the solution was stirred at room temperature for 1 hour. The reaction mixture was treated according to Process C, and crude crystals obtained were recrystallized from a mixed solvent of methanol/ether/hexane. Yield, 11.8 g (93.2%).

Characteristics of the product: m.p., 193° to 195° C. (decomposition); $[\alpha]_D^{16.5}$ −11.2° (c 1.00, DMF).

Elementary analysis:

Found: C, 60.26; H, 5.68; N, 6.86; Cl, 11.61%. Calculated as $C_{31}H_{35}N_3O_6Cl_2$: C, 60.39; H, 5.72; N, 6.82; Cl, 11.50%.

EXPERIMENT 3

Preparation of Boc-Ile-Phe-Lys(ClZ)-OPac (3)

HCl.H-Phe-Lys(ClZ)-OPac (2) (10.5 g, 17 mmol) obtained in Experiment 2 was dissolved in 90 ml of DMF, and triethylamine (2.39 ml, 17 mmol) was added under ice cooling. Thereafter, Boc-Ile-OSu (5.59 g, 17 mmol) was added, followed by stirring overnight. N-(2-aminoethyl)-piperazine (0.45 ml, 3.4 mmol) was added, followed by stirring under ice cooling for 30 minutes. The resulting reaction mixture was subjected to treatment by Process A, and a crude product obtained was recrystallized from a mixed solvent of methanol/ether/hexane. Yield, 9.15 g (67.8%).

Characteristics of the product: m.p., 178°–179° C.; $[\alpha]_D^{17}$ −14.4° (c 0.98, DMF).

Elementary analysis: Found: C, 63.50; H, 6.75; N, 7.02; Cl, 4.44%. Calculated as $C_{42}H_{53}N_4O_9Cl$: C, 63.59; H, 6.73; N, 7.06; Cl, 4.47%.

EXPERIMENT 4

Preparation of HCl.H-Ile-Phe-Lys(ClZ)-OPac (4)

Boc-Phe-Lys(ClZ)-OPac (3) (7.93 g, 20 mmol) obtained in Experiment 3 was dissolved in 175 ml of 1.15N HCl in AcOH, and the solution was stirred at room temperature for 40 minutes. The reaction mixture obtained was treated according to Process C, and crude crystals obtained were recrystallized from a mixed solvent of methanol/ether. Yield, 7.29 g (100%).

Characteristics of the product: m.p., 210° to 213° C. (decomposition); $[\alpha]_D^{14.5}$ +11.0° (c 1.01, DMSO).

Elementary analysis: Found: C, 60.67; H, 6.35; N, 7.57; Cl, 9.76%. Calculated as $C_{37}H_{46}N_4O_7Cl_2$: C, 60.90; H, 6.35; N, 7.68; Cl, 9.72%.

EXPERIMENT 5

Preparation of Boc-Lys(ClZ)-Ile-Phe-Lys(ClZ)-OPac (5)

HCl.H-Ile-Phe-Lys(ClZ)-OPac (4) (6.51 g, 8.92 mmol) obtained in Experiment 4 was dissolved in 55 ml of DMF, and triethylamine (1.25 ml, 8.92 mmol) and Boc-Lys(ClZ)-OSu (4.57 g, 8.92 mmol) were added under ice cooling, followed by stirring overnight at room temperature. N-(2-aminoethyl)-piperazine (0.23 ml, 1.78 mmol) was added, followed by stirring under ice cooling for 30 minutes. The resulting reaction mixture was subjected to treatment by Process B to obtain a desired peptide. Yield, 9.59 g (98.6%).

Characteristics of the product: m.p., 188.5°–190° C.; $[\alpha]_D^{16}$ −15.9° (c 0.98, DMSO).

Elementary analysis: Found: C, 61.31; H, 6.45; N, 7.68; Cl, 6.57%. Calculated as $C_{56}H_{70}N_6O_{12}Cl_2.0.5-H_2O$: C, 61.20; H, 6.51; N, 7.65; Cl, 6.45%.

EXPERIMENT 6

Preparation of HCl.H-Lys(ClZ)-Ile-Phe-Lys(ClZ)-OPac (6)

Boc-Lys(ClZ)-Ile-Phe-Lys(ClZ)-OPac (5) (9.00 g, 8.26 mmol) obtained in Experiment 5 was dissolved in 140 ml of 1.2N HCl in AcOH, and the solution was stirred at room temperature for 3 hours. The reaction mixture obtained was treated according to Process C, and a crude product obtained was precipitated from a mixed solvent of methanol/ether. Yield, 8.23 g (97.2%).

Characteristics of the product: m.p., 203° to 205° C. (decomposition); $[\alpha]_D^{16}$ −4.4° (c 1.02, DMSO).

Elementary analysis: Found: C, 58.60; H, 6.21; N, 8.04; Cl, 10.49%. Calculated as $C_{51}H_{63}N_6O_{10}Cl_3$: C, 58.60; H, 6.27; N, 8.05; Cl, 10.18%.

EXPERIMENT 7

Preparation of Boc-Trp(CHO)-Lys(ClZ)-Ile-Phe-Lys(ClZ)-OPac (7)

HCl.H-Lys(ClZ)-Ile-Phe-Lys(ClZ)-OPac (6) (3.09 g, 3 mmol) obtained in Experiment 6 was dissolved in 30 ml of DMF, and triethylamine (423 μl, 3 mmol) and Boc-Trp(CHO)-OSu (1.55 g, 3.6 mmol) were added under ice cooling, followed by stirring for 2 days at room temperature. The resulting reaction mixture was subjected to treatment by Process B, and a crude product obtained was reprecipitated from a mixed solvent of DMF/AcOEt/ether. Yield, 3.21 g (81.7%).

Characteristics of the product: m.p., 221.5° to 222.5° C. (decomposition); $[\alpha]_D^{17}$ −11.4° (c 0.99, DMSO).

Elementary analysis: Found: C, 62.47; H, 6.16; N, 8.63; Cl, 5.43%. Calculated as $C_{68}H_{80}N_8O_{14}Cl_2$: C, 62.62; H, 6.18; N, 8.59; Cl, 5.44%.

EXPERIMENT 8

Preparation of TFA.H-Trp(CHO)-Lys(ClZ)-Ile-Phe-Lys(ClZ)-OPac (8)

Boc-Trp(CHO)-Lys(ClZ)-Ile-Phe-Lys(ClZ)-OPac (7) (1.50 g, 1.15 mmol) obtained in Experiment 7 was dissolved in 35 ml of a mixed solvent of TFA/dimethyl sulfide/1,2-ethanediol (10:10:1 v/v) under ice cooling, followed by stirring for 2 hours at room temperature. The resulting reaction mixture was subjected to treatment by Process C, and a precipitate obtained was reprecipitated from a mixed solvent of DMF/AcOEt. Yield, 1.28 g (83.9%).

EXPERIMENT 9

Preparation of Boc-Arg(Tos)-Trp(CHO)-Lys(ClZ)-Ile-Phe-Lys(ClZ)-OPac (9)

TFA.H-Trp(CHO)-Lys(ClZ)-Ile-Phe-Lys(ClZ)-OPac (8) (1.28 g, 0.967 mmol) obtained in Experiment 8 was dissolved in 15 ml of DMF, and triethylamine (136 μl, 0.967 mmol) and Boc-Arg(Tos)-OSu (1.02 g, 1.93 mmol) were added under ice cooling, followed by stirring overnight at room temperature. The resulting reaction mixture was subjected to treatment by Process B, and a crude product obtained was reprecipitated from a mixed solvent of DMF/methanol. Yield, 1.20 g (76.8%).

Characteristics of the product: m.p., 191° to 194° C. (decomposition); $[\alpha]_D^{17}$ −10.5° (c 0.99, DMSO).

Elementary analysis: Found: C, 59.89; H, 6.15; N, 10.45; S, 2.04; Cl, 4.23%. Calculated as $C_{81}H_{98}N_{12}O_{17}SCl_2 \cdot 0.5H_2O$: C, 59.92; H, 6.15; N, 10.35; S, 1.97; Cl, 4.37%.

Amino acid analysis (Condition II): Ile 0.89(1), Phe 0.91(1), Lys 2.00(2), Trp 0(1), Arg 0.92 (1).

The substance obtained in Experiment 9 is hereinafter abridged as Boc-(1–6)$_p$-OPac.

EXPERIMENT 10

Preparation of Boc-Met-Gly-OPac (10)

HCl.H-Gly-OPac (6.89 g, 30 mmol) and Boc-Met-OSu (10.39 g, 30 mmol) were dissolved in 140 ml of DMF, and triethylamine (4.21 ml, 30 mmol) was added to the solution in three installments and over one hour under ice cooling, followed by stirring overnight at room temperature. N-(2-aminoethyl)-piperazine (0.79 ml, 6 mmol) was further added, followed by stirring under ice cooling for 30 minutes. The resulting reaction mixture was subjected to treatment by Process A, and crude crystals obtained were recrystallized from a mixed solvent of AcOEt/hexane. Yield, 10.3 g (1.2%).

Characteristics of the product: m.p., 84°–86° C.; $[\alpha]_D^{15.5}$ −17.8° (c 1.02, DMF).

Elementary analysis: Found: C, 56.65; H, 6.61; N, 6.63; S, 7.64%. Calculated as $C_{20}H_{28}N_2O_6S$: C, 56.59; H, 6.65; N, 6.60; S, 7.55%.

EXPERIMENT 11

Preparation of HCl.H-Met-Gly-OPac (11)

Boc-Met-Gly-OPac (10) (2.00 g, 4.71 mmol) obtained in Experiment 10 was dissolved in 25 ml of 4.2N HCl in THF, and the solution was stirred for 1 hour at room temperature. The resulting reaction mixture was treated according to Process C, and a crude product obtained was recrystallized from a mixed solvent of methanol/ether. Yield, 1.60 g (94.1%).

Characteristics of the product: m.p., 168°–170° C. (decomposition); $[\alpha]_D^{16}$ +9.8° (c 1.01, DMF).

Elementary analysis: Found: C, 49.84; H, 5.88; N, 7.75; S, 9.07; Cl, 9.91%. Calculated as $C_{15}H_{21}N_2O_4SCl$: C, 49.93; H, 5.87; N, 7.76; S, 8.88; Cl, 9.82%.

EXPERIMENT 12

Preparation of Boc-Lys(ClZ)-Met-Gly-OPac (12)

HCl.H-Met-Gly-OPac (11) (6.00 g, 16.6 mmol) obtained in Experiment 11 and Boc-Lys(ClZ)-OSu (10.0 g, 19.5 mmol) were dissolved in 90 ml of DMF, and triethylamine (2.33 ml, 16.6 mmol) was added under ice cooling, followed by stirring for 40 hours at room temperature. The resulting reaction mixture was subjected to treatment by Process A, and a crude product obtained was reprecipitated from a mixed solvent of methanol/ether/hexane. Yield, 11.07 g (92.3%).

Characteristics of the product: m.p., 138.5°–140° C.; $[\alpha]_D^{16}$ −16.3° (c 1.00, DMF).

Elementary analysis: Found: C, 56.57; H, 6.26; N, 7.76; S, 4.56; Cl, 5.08%. Calculated as $C_{34}H_{45}N_4O_9SCl$: C, 56.62; H, 6.29; N, 7.77; S, 4.44; Cl, 4.92%.

EXPERIMENT 13

Preparation of HCl.H-Lys(ClZ)-Met-Gly-OPac (13)

Boc-Lys(ClZ)-Met-Gly-OPac (12) (1.25 g, 1.73 mmol obtained in Experiment 12 was dissolved in 35 ml of 1N HCl in AcOH, and the solution was stirred for 30 minutes at room temperature. The resulting reaction mixture was treated according to Process C, and a precipitate obtained was reprecipitated from a mixed solvent of methanol/ether. Yield, 1.01 g (88.6%).

Characteristics of the product: m.p., 186° to 188° C. (decomposition); $[\alpha]_D^{16}$ −4.9° (c 1.03, DMF).

Elementary analysis: Found: C, 52.56; H, 5.78; N, 8.45; S, 4.83; Cl, 10.86%. Calculated as $C_{29}H_{38}N_4O_7SCl_2 \cdot 0.5H_2O$: C, 52.25; H, 5.90; N, 8.40; S, 4.81; Cl, 10.63%.

EXPERIMENT 14

Preparation of Boc-Glu(OBzl)-Lyz(ClZ)-Met-Gly-OPac (14)

HCl.H-Lys(ClZ)-Met-Gly-OPac (13) (800 mg, 1.22 mmol) obtained in Experiment 13 was dissolved in 7 ml of DMF, and triethylamine (171 μl, 1.22 mmol) and Boc-Glu(OBzl)-OSu (528 mg, 1.22 mmol) were added under ice cooling, followed by stirring overnight at room temperature. N-(2-aminoethyl)-piperazine (32 μl, 0.25 mmol) was further added, followed by stirring under ice cooling for 30 minutes. The resulting reaction mixture was subjected to treatment by Process A, and a precipitate obtained was reprecipitated from a mixed solvent of methanol/ether. Yield, 0.98 g (85.9%).

Characteristics of the product: m.p., 164°–166° C.; $[\alpha]_D^{16}$ −12.9° (c 1.01, DMF).

Elementary analysis: Found: C, 58.53; H, 6.21; N, 7.53; S, 3.37; Cl, 3.81%. Calculated as $C_{46}H_{58}N_5O_{12}SCl$: C, 58.75; H, 6.22; N, 7.45; S, 3.41; Cl, 3.77%.

EXPERIMENT 15

Preparation of HCl.H-Glu(OBzl)-Lys(ClZ)-Met-Gly-OPac (15)

Boc-Glu(OBzl)-Lys(ClZ)-Met-Gly-OPac (14) (9.50 g, 10.1 mmol) obtained in Experiment 14 was dissolved in 180 ml of 1.2N HCl in AcOH, and the solution was stirred for 2 hours at room temperature. The resulting reaction mixture was treated according to Process C, and crude crystals obtained were reprecipitated from a mixed solvent of methanol/ether. Yield, 7.35 g (82.9%).

Characteristics of the product: m.p., 173° to 175° C. (decomposition); $[\alpha]_D^{16} +1.2°$ (c 1.01, DMSO).

Elementary analysis: Found: C, 55.07; H, 5.84; N, 8.03; S, 3.81; Cl, 8.17%. Calculated as $C_{41}H_{51}N_5O_{10}SCl_2.H_2O$: C, 55.03; H, 5.97; N, 7.83; S, 3.58; Cl, 7.92%.

EXPERIMENT 16

Preparation of Boc-Ile-Glu(OBzl)-Lys(ClZ)-Met-Gly-OPac (16)

HCl.H-Glu(OBzl)-Lys(ClZ)-Met-Gly-OPac (15) (6.50 g, 7.41 mmol) obtained in Experiment 15 and Boc-Ile-OSu (2.92 g, 8.90 mmol) were dissolved in 55 ml of DMF, and triethylamine (1.04 ml, 7.41 mmol) was added under ice cooling, followed by stirring overnight at room temperature. The resulting reaction mixture was subjected to treatment by Process B, and a crude product obtained was reprecipitated from a mixed solvent of methanol/ether/hexane. Yield, 6.37 g (81.6%).

Characteristics of the product: m.p., 178° C. (half-molten), 180°-182° C.; $[\alpha]_D^{16.5} -10.8°$ (c 0.99, DMSO).

Elementary analysis: Found: C, 59.11; H, 6.60; N, 7.93; S, 3.25; Cl, 3.29%. Calculated as $C_{52}H_{69}N_6O_{13}SCl$: C, 59.28; H, 6.60; N, 7.98; S, 3.04; Cl, 3.36%.

EXPERIMENT 17

Preparation of HCl.H-Ile-Glu(OBzl)-Lys(ClZ)-Met-Gly-OPac (17)

Boc-Ile-Glu(OBzl)-Lys(ClZ)-Met-Gly-OPac (16) (6.00 g, 5.69 mmol) obtained in Experiment 16 was dissolved in 85 ml of 1.4N HCl in AcOH, and the solution was stirred for 90 minutes at room temperature. The resulting reaction mixture was treated according to Process C, and a precipitate obtained were reprecipitated from a mixed solvent of methanol/ether. Yield, 5.45 g (96.6%).

Characteristics of the product: m.p., 208° to 209.5° C. (decomposition); $[\alpha]_D^{16.5}+1.1°$ (c 1.02, DMSO).

Elementary analysis: Found: C, 56.38; H, 6.32; N, 8.40; S, 3.35; Cl, 6.93%. Calculated as $C_{47}H_{62}N_6O_{11}SCl_2.0.5H_2O$: C, 56.50; H, 6.36; N, 8.41; S, 3.21; Cl, 7.10%.

EXPERIMENT 18

Preparation of Boc-Lys(ClZ)-Ile-Glu(OBzl)-Lys(ClZ)-Met-Gly-OPac (18)

HCl.H-Ile-Glu(OBzl)-Lys(ClZ)-Met-Gly-OPac (17) (4.60 g, 4.65 mmol) obtained in Experiment 17 and Boc-Lys(ClZ)-OSu (2.62 g, 5.11 mmol) were dissolved in 50 ml of DMF, and triethylamine (652 μl, 4.65 mmol) was added under ice cooling, followed by stirring overnight at room temperature. N-(2-aminoethyl)-piperazine (122 μl, 0.93 mmol) was further added, followed by stirring under ice cooling for 30 minutes. The resulting reaction mixture was subjected to treatment by Process B, and a precipitate obtained was reprecipitated from a mixed solvent of methanol/AcOEt/ether. Yield, 5.49 g (87.5%).

Characteristics of the product: m.p., 173° C. (half-motion); 204° to 206° C. (decomposition); $[\alpha]_D^{16.5} -13.7°$ (c 0.98, DMSO).

Elementary analysis: Found: C, 58.26; H, 6.39; N, 8.26; s, 2.37; Cl, 5.11%. Calculated as $C_{66}H_{86}N_8O_{16}SCl_2.0.5H_2O$: C, 58.31; H, 6.45; N, 8.24; S, 2.36; Cl, 5.22%.

Amino acid analysis: Glu 1.01(1), Gly 1.00(1), Met 0.89(1), Ile 0.95(1), Lys 2.08(2) (6M hydrochloric acid, 110° C., 48 hours).

The substance obtained in Experiment 18 is hereinafter abridged as Boc-(7-12))$_p$—OPac.

EXPERIMENT 19

Preparation of Boc-Asp(OcHex)-Gly-Opac (19)

HCl.H-Gly-OPac (2.00 g, 8.72 mmol) and Boc-Asp(OcHex)-OH (2.50 g, 7.93 mmol) were suspended in 45 ml of THF, and N,N-diisobutylethylamine (1.52 ml, 8.73 mmol) and DCC (1.64 g, 7/95 mmol) were added under ice cooling, followed by stirring for 6 hours at room temperature. Dicyclohexyl urea precipitated was filtered off, and the reaction mixture was treated by Process A to obtain an oily product. Yield, 3.25 g (83.5%).

Characteristics of the product: $[\alpha]_D^{15} -15.9°$ (c 1.23, DMF).

Elementary analysis: Found: C, 61.11; H, 6.93; N, 5.62%. Calculated as $C_{25}H_{34}N_2O_8$: C, 61.21; H, 6.99; N, 5.71%.

EXPERIMENT 20

Preparation of HCl.H-Asp(OcHex)-Gly-OPac (20)

Boc-Asp(OcHex)-Gly-OPac (19) (2.99 g, 6.10 mmol) obtained in Experiment 19 was dissolved in 30 ml of 4.23N HCl in THF, and the solution was stirred for 60 minutes at room temperature. The resulting reaction mixture was treated according to Process C, and a crude product obtained was recrystallized from a mixed solvent of methanol/ether. Yield, 2.48 g (95.4%).

EXPERIMENT 21

Preparation of Boc-Arg(Tos)-Asp(OcHex)-Gly-OPac (21)

HCl.H-Asp(OcHex)-Gly-OPac (20) (10.7 g, 25.1 mmol) obtained in Experiment 20 was dissolved in 150 ml of THF, followed by addition of HOBt (3.39 g, 25.1 mmol), Boc-Arg(Tos)-OH.1/3AcOEt (11.5 g, 25.1 mmol) and N,N-diisobutylethylamine (4.37 ml, 25.1 mmol) under ice cooling, and thereafter DCC (5.18 g, 25.1 mmol) was added, followed by stirring overnight. Dicyclohexyl urea was filtered off from the resulting reaction mixture, which was then treated by Process A to obtain a crude product. This was purified by silica gel chromatography (7×24 cm; benzene/AcOEt=1:3). Yield, 15.3 g (76.1%).

Characteristics of the product: m.p., 75°-77° C.; $[\alpha]_D^{15.5} -11.8°$ (c 0.95, DMF).

Elementary analysis: Found: C, 56.88; H, 6.76; N, 10.25; S, 3.93%. Calculated as $C_{38}H_{52}N_6O_{11}S$: C, 56.99; H, 6.54; N, 10.49; S, 4.00%.

EXPERIMENT 22

Preparation of
HCl.H-Arg(Tos)-Asp(OcHex)-Gly-OPac (22)

Boc-Arg(Tos)-Asp(OcHex)-Gly-OPac (21) (1.43 g, 17.9 mmol) obtained in Experiment 21 was dissolved in 70 ml of 5.26N HCl in THF, and th solution was stirred for 1 hour at room temperature. The resulting reaction mixture was treated according to Process C to obtain hydroscopic crystals. Yield, 1.18 g (100%).

EXPERIMENT 23

Preparation of
Boc-Ile-Arg(Tos)-Asp(OcHex)-Gly-OPac (23)

HCl.H-Arg(Tos)-Asp(OcHex)-Gly-Opac (22) (13.2 g, 17.9 mmol), HOBt (2.42 g, 17.9 mmol) and Boc-Ile-OPac (16.6 g, 34.6 mmol) were dissolved in 10 ml of THF, and N,N-diisobutylamine (6.24 ml, 35.8 mmol) was added to the solution in three installments and over one hour under ice cooling, followed by stirring for 5 hours at room temperature. The resulting reaction mixture was subjected to treatment by Process A, and a crude product obtained was reprecipitated from a mixed solvent of THF/ether. Yield, 15.9 g (96.8%).

Characteristics of the product: m.p., 93° to 95° C. (decomposition); $[\alpha]_D^{16} -16.7°$ (c 1.00, DMF).

Elementary analysis: Found: C, 56.98; H, 6.89; N, 10.68; S, 3.68%. Calculated as $C_{44}H_{63}N_7O_{12}S \cdot H_2O$: C, 56.70; H, 7.03; N, 10.52; S, 3.44%.

EXPERIMENT 24

Preparation of
HCl-H-Ile-Arg(Tos)-Asp(OcHex)-Gly-OPac (24)

Boc-Ile-Arg(Tos)-Asp(OcHex)-Gly-OPac (23) (1.31 g, 1.44 mmol) obtained in Experiment 23 was dissolved in 8 ml of 4.23N HCl in THF, and the solution was stirred for 150 minutes at room temperature. The resulting reaction mixture was treated according to Process C to obtain hygroscopic crystals. Yield, 1.21 g (98.5%).

EXPERIMENT 25

Preparation of
Boc-Asn-Ile-Arg(Tos)-Asp(OcHex)-Gly-OPac (25)

HCl.H-Ile-Arg(Tos)-Asp(OcHex)-Gly-OPac (24) (8.04 g, 9.45 mmol) obtained in Experiment 24, HOBt (1.41 g, 10.4 mmol) and Boc-Asn-ONp (3.67 g, 10.4 mmol) were dissolved in 70 ml of DMF, and N,N-diisobutylamine (872 µl, 6.20 mmol) was added to the solution in three installments and over 20 minutes under ice cooling, followed by stirring for 2 hours at room temperature. The resulting reaction mixture was subjected to treatment by Process B, and a crude product obtained was washed with methanol. Yield, 7.79 g (80.2%).

Characteristics of the product: m.p., 187°-190° C.; $[\alpha]_D^{16} -19.5°$ (c 1.03, DMF).

Elementary analysis: Found: C, 54.89; H, 6.79; N, 12.01; S, 3.04%. Calculated as $C_{48}H_{69}N_9O_{14}S \cdot H_2O$: C, 55.11; H, 6.84; N, 12.05; S, 3.04%.

EXPERIMENT 26

Preparation of
HCl.H-Asn-Ile-Arg(Tos)-Asp(OcHex)-Gly-OPac (26)

Boc-Asn-Ile-Arg(Tos)-Asp(OcHex)-Gly-OPac (25) (6.17 g, 6.00 mmol) obtained in Experiment 25 was dissolved in 100 ml of 1.4N HCl in AcOH, and the solution was stirred at room temperature for 2 hours. The resulting reaction mixture was treated according to Process C to obtain a desired product. Yield, 5.7 g (quantitative).

EXPERIMENT 27

Preparation of
Boc-Arg(Tos)-Asn-Ile-Arg(Tos)-Asp(OcHex)-Gly-OPac (27)

HCl.H-Asn-Ile-Arg(Tos)-Asp(OcHex)-Gly-OPac (26) (1.35 g, 1.40 mmol) obtained in Experiment 26 was dissolved in 50 ml of DMF, HOBt (189 mg, 1.40 mmol) and Boc-Arg(Tos)-OSu (1.47 g, 2.80 mmol) were added and dissolved, and N,N-diisobutylamine (244 µl, 1.40 mmol) was added under ice cooling, followed by stirring for 4 days at room temperature. N,N-diisobutylamine (341 µl, 1.96 mmol) was further added, followed by stirring overnight at room temperature. The resulting reaction mixture was subjected to treatment by Process B, and a crude product obtained was reprecipitated from a mixed solvent of THF/ether. Yield, 1.51 g (80.7%).

Characteristics of the product: m.p., 170° C. (half-molten), 184°-186.5° C.; $[\alpha]_D^{16.5} -16.7°$ (c 0.97, DMF).

Elementary analysis: Found: C, 53.27; H, 6.50; N, 13.26; S, 4.72%. Calculated as $C_{61}H_{87}N_{13}O_{17}S_2 \cdot 2H_2O$: C, 53.30; , 6.67; N, 13.25; S, 4.66%.

Amino acid analysis (Condition II): Asp 1.86(2), Gly 1.00(1), Ile 0.88(1), Arg 1.64(2).

The substance obtained in Experiment 27 is hereinafter abridged as Boc-(13-18)$_p$—OPac.

EXPERIMENT 28

Preparation of Boc-(1-6)$_p$—OH

Preparation of
Boc-Arg(Tos)-Trp(CHO)-Lys(ClZ)-Ile-Phe-Lys(ClZ)-OH (28)

Boc-(1-6)$_p$—OPac (9) (699 mg, 0.433 mmol) obtained in Experiment 9 was dissolved in 20 ml of a mixed solvent of DMSO/AcOH (1:1 v/v), and zinc powder (1.45 g, 22 mmol) was added, followed by stirring for 2 hours at room temperature. The resulting reaction mixture was treated by Process E to obtain a desired product. Yield, 609 mg (94.0%).

EXPERIMENT 29

Preparation of H—(7-12)$_p$—OPac

Preparation of
HCl.H-Lys(ClZ)-Ile-Glu(OBzl)-Lys(ClZ)-Met-Gly-OPac (29)

Boc—(7-12)$_p$—OPac (18) (1.35 g, 1.00 ml) obtained in Experiment 18 was dissolved in 25 ml of 1.4N HCl in AcOH, followed by stirring for 20 minutes at room temperature. The resulting reaction mixture was treated by Process C to obtain a desired product. Yield, 1.24 g (97.1%).

EXPERIMENT 30

Preparation of Boc—(1-12)$_p$—OPac

Preparation of
Boc-Arg(Tos)-Trp(CHO)-Lys(ClZ)-Ile-Phe-Lys(ClZ)-Lys-(ClZ)-Ile-Glu(OBzl)-Lys(ClZ)-Met-Gly-OPac (30)

HCl.H—(7-12)$_p$—OPac (29) (497 mg, 0.386 mmol) obtained in Experiment 29, HOBt (52.2 mg, 0.386 mmol) and Boc—(1-6)$_p$—OH (28) (578 mg, 0.386 mmol) obtained in Experiment 28 was dissolved in 15 ml of DMF, and WSCI (60 μl, 0.386 mmol) was added under cooling at −70° C., followed by stirring overnight at room temperature. The resulting reaction mixture was treated by Process B, and a crude product obtained was reprecipitated from a mixed solvent of DMF/methanol. Yield, 812 mg (77.0 %).

Characteristics of the product: m.p., 200° C. (decomposition with coloring); $[\alpha]_D^{28}$ −8.9° (c 1.00, NMP).

Elementary analysis: Found: C, 58.55; H, 6.21; N, 10.23; S, 2.47; Cl, 5.06%. Calculated as $C_{134}H_{168}N_{20}O_{29}S_2Cl_4 \cdot H_2O$: C, 58.59; H, 6.24; N, 10.20; S, 2.33; Cl, 5.16%.

Amino acid analysis (Condition II):
Glu 0.95(1), Gly 1.00(1), Met 0.64(1), Ile (1.81)2, Phe 0.85(1), Lys 3.92(4), Trp 0(1), Arg 0.81(1).

EXPERIMENT 31

Preparation of Boc-(1-12)$_p$—OH

Preparation of
Boc-Arg(Tos)-Trp(CHO)-Lys(ClZ)-Ile-Phe-Lys(ClZ)-Lys(ClZ)-Ile-Glu(OBzl)-Lys(ClZ)-Met-Gly-OH (31)

Boc-(1-12)$_p$—OPac (30) (812 mg, 0.297 mmol) obtained in Experiment 30 was dissolved in 25 ml of a mixed solvent of NMP/AcOH (5:1 v/v), and zinc powder (5.29 g, 80.9 mmol) was added, followed by stirring for 24 hours at room temperature. The resulting reaction mixture was treated by Process F to obtain a desired product. Yield, 698 mg (89.8%).

EXPERIMENT 32

Preparation of H—(13-18)$_p$—OPac

Preparation of
HCl.H-Arg(Tos)-Asn-Ile-Arg(Tos)-Asp(OcHex)-Gly-OPac (32)

Boc-(13-18)$_p$—OPac (27) (250 mg, 0.186 mmol) obtained in Experiment 27 was dissolved in 5 ml of 1.4N HCl in AcOH, and the solution was stirred for 1 hour at room temperature. The resulting reaction mixture was treated according to Process C to obtain a hygroscopic precipitate. Yield, 227 mg (95.4%).

EXPERIMENT 33

Preparation of Boc-(1-18)$_p$—OPac

Preparation of
Boc-Arg(Tos)-Trp(CHO)-Lys(ClZ)-Ile-Phe-Lys(ClZ)-Lys(ClZ)-Ile-Glu(OBzl)-Lys(ClZ)-Met-Gly-Arg(Tos)-Asn-Ile-Arg(Tos)-Asp(OcHex)-Gly-OPac (33)

HCl.H—(13-18)$_p$—OPac (32) (130 mg,. 0.102 mmol) obtained in Experiment 32 was dissolved in 6 ml of a mixed solvent of DMF/DMSO (1:1 v/v), N,N-diisopropylamine (DIEA) (17.7 μl, 0.102 mmol), HOBt (13.7 mg, 0.102 mmol) and Boc—(1-12)$_p$—OH (31) (266 mg,. 0.102 mmol) obtained in Experiment 31 were added and dissolved, and WACI.HCl (19.5 mg, 0.102 mmol) was further added under ice cooling to proceed reaction at room temperature, followed by stirring for 7 days at room temperature while adding at appropriate intervals DIEA (17.7 μl in total) and WACI.HCl (9.8 mg) until HCl.H—(13-18)$_p$—OPac disappeared. The resulting reaction mixture was subjected to gel filtration using Sephadex LH-60 (2.5×70 cm; DMF/DMSO/AcOH=20:20:1; 15 ml/hr) as a carrier. Absorption of the respective fractions at the wavelength of 320 nm was monitored to obtain the elution pattern as shown in FIG. 1. The fractions corresponding to fractions 42 to 67 were collected, and a precipitate formed by adding water to these was collected by centrifugal sedimentation, and washed with water, THF and ether. Yield, 235 mg (60.3%).

Characteristics of the product: m.p., 226° C. (decomposition); $[\alpha]_D^{29}$ −9.1° (c 1.04, NMP).

Elementary analysis: Found: C, 55.96; H, 6.34; N, 11.51; S, 4.22; Cl, 3.80%. Calculated as $C_{182}H_{239}N_{33}O_{42}S_4Cl_4 \cdot 5H_2O$: c, 55.75; H, 6.40; N, 11.79; S, 3.27; Cl, 3.62%.

Amino acid analysis (Condition II): Asp 1.75(2), Glu 1.08(1), Gly 2.00(2), Met 0.74(1), Ile 2.96(3), Phe 1.01(1), Lys 4.41(4), Trp 0(1), Arg 2.68(3).

EXPERIMENT 34

Preparation of Boc-(1-18)$_p$—OH

Preparation of
Boc-Arg(Tos)-Trp(CHO)-Lys(ClZ)-Ile-Phe-Lys(ClZ)-Lys(ClZ)-Ile-Glu(OBzl)-Lys(ClZ)-Met-Gly-Arg(Tos)-Asn-Ile-Arg(Tos)-Asp(OcHex)-Gly-OH (34)

Boc—(1-18)$_p$—OPac (33) (185 mg, 48.2 μmol) obtained in Experiment 33 was dissolved in 10 ml of a mixed solvent of DMSO/AcOH (4:1 v/v), and zinc powder (1.40 g, 21.4 mmol) was added at appropriate intervals, followed by stirring for 3 days at room temperature. The resulting reaction mixture was treated by Process F to obtain a desired product. Yield, 176 mg (98.5%).

II. PREPARATION EXAMPLES FOR ANTIBACTERIAL SUBSTANCE OF THE INVENTION (EXPERIMENTS 35 TO 42)

EXPERIMENT 35

Preparation of H—(1-18)—NH(CH$_2$)$_{11}$CH$_3$.8HCl (1) Boc—(1-18)$_p$—OH (34) (200 mg, 53.9 μmol) obtained in Experiment 34 was dissolved in a mixed solvent (4 ml) of DMSO/NMP/DMF (1:1:1), CH$_3$(CH$_2$)$_{11}$NH$_2$ (10.0 mg, 53.9 μmol) was HOBt (7.3 mg, 53.9 μmol) were added, and WSCI.HCl (10.3 mg, 53.9 μmol) were further added under ice cooling. After return to room temperature, the reaction was carried out for 18 hours. After a ninhydrin reaction test was carried out on the reaction mixture to confirm that it turned negative, CH$_3$(CH$_2$)$_{11}$NH$_2$ (2.0 mg, 10.8 μmol) and WSCI.HCl (2.1 mg, 10.8 μmol) were added thereto and the reaction was carried out for 5 hours. Subsequently, the reaction mixture was subjected to post-treatment by Process B. Yield, 155 mg (74.1%).

(2) The product thus obtained (70 mg, 18.0 μmol) was put into an HF reaction tube, and dissolved in TFA (5 ml), followed by stirring for 1 hour at room temperature. After evaporation of TFA, the content was dried over NaOH in a desiccator. Anisole (560 μl) was poured into the reaction tube, which was cooled to −70° C., and thereafter 5 ml of HF were introduced into it, followed by stirring for 1 hour at 0° C. After HF was evaporated under reduced pressure (0° C., 25 minutes), 2.5 ml of 1,2-ethanediol (EDT) were poured into the reaction tube, and then 2.5 ml of HF were again introduced into it, followed by stirring for 30 minutes at 0° C. HF was evaporated under reduced pressure (0° C., 30 minutes), and 4% AcOH was added to the residue, followed by washing with ether.

The aqueous layer was passed through a column of an ion-exchange resin (trade name Dowex 1×8, AcO⁻ type, 12×280 mm) to collect ninhydrin-positive fractions, which were freeze-dried to obtain a crude product. This product was purified by high pressure liquid chromatography (HPLC) (Nucleosil 300 −7$C_{18}$, 6×250 mm, gradient elution from 30% $CH_3CN$/0.1% TFA to 60% $CH_3CN$/0.1% TFA). The resulting product was freeze-dried to obtain white powder. Yield, 12.8 mg (26.0%).

Characteristics of the product: FAB-MS M+H: 2441 (Calcd. 2441).

UV Absorption: λ(shoulder), 287 nm; λmax 280 nm.

EXPERIMENT 36

Preparation of H—(1-18)—NH($CH_2$)$_{13}$$CH_3$.8HCl

Condensation was carried out in the same manner as in (1) of Experiment 35 except that $CH_3(CH_2)_{13}NH_2$ (11.5 mg, 53.9 μmol) was used in place of $CH_3(CH_2)_{11}NH_2$. Yield, 156 mg (74.1%).

A 80 mg portion of the product obtained in the above was unblocked and purified in the same manner as in (2) of Experiment 35 to obtain the entitled end product. Yield, 16.8 mg (29.7%).

Characteristics of the product: FAB-MS M+H: 2469 (Calcd. 2469).

UV Absorption: λ(shoulder), 287 nm; λmax 280 nm.

EXPERIMENT 37

Preparation of H—(1-18(—NH($CH_2$)$_{15}$$CH_3$.8HCl

Condensation was carried out in the same manner as in (1) of Experiment 35 except that $CH_3(CH_2)_{15}NH_2$ (13.0 mg, 53.9 μmol) was used in place of $CH_3(CH_2)_{11}NH_2$. Yield, 210 mg (98.9%).

A 100 mg portion of the product obtained in the above was unblocked and purified in the same manner as in (2) of Experiment 35 to obtain the entitled end product. Yield, 20.3 mg (28.6%).

Characteristics of the product: FAB-MS M+H; 2497 (Calcd. 2497).

UV Absorption: λ(shoulder), 287 nm; λmax 280 nm.

EXPERIMENT 38

Preparation of H—(1-18)—NH($CH_2$)$_9$$CH_3$.8HCl

Condensation was carried out in the same manner as in (1) of Experiment 35 except that $CH_3(CH_2)_9NH_2$ (8.5 mg, 53.9 μmol) was used in place of $CH_3(CH_2)_{11}NH_2$. Yield, 204 mg (98.6%).

A 100 mg portion of the product obtained in the above was unblocked and purified in the same manner as in (2) of Experiment 35 to obtain the entitled end product. Yield, 18.4 mg (29.2%).

Characteristics of the product: FAB-MS M+H: 2413 (Calcd. 2413).

UV Absorption: λ(shoulder), 287 nml λmax 280 nm.

EXPERIMENT 39

Preparation of H—(1-18)—NH($CH_2$)$_7$$CH_3$.8HCl

Condensation was carried out in the same manner as in (1) of Experiment 35 except that $CH_3(CH_2)_7NH_2$ (6.9 mg, 53.9 μmol) was used in place of $CH_3(CH_2)_{11}NH_2$. Yield, 203 mg (98.4%).

A 80 mg portion of the product obtained in the above was unblocked and purified in the same manner as in (2) of Experiment 35 to obtain the entitled end product. Yield, 16.2 mg (28.2%).

Characteristics of the product: FAB-MS M+H: 2385 (Calcd. 2385).

UV Absorption: λ(shoulder), 287 nm; λmax 280 nm.

EXPERIMENT 40

Preparation of H—(1-18)—NH($CH_2$)$_5$$CH_3$.8HCl

Condensation was carried out in the same manner as in (1) of Experiment 35 except that $CH_3(CH_2)_5NH_2$ (5.4 mg, 53.9 μmol) was used in place of $CH_3(CH_2)_{11}NH_2$. Yield, 201 mg (98.0%).

A 100 mg portion of the product obtained in the above was unblocked and purified in the same manner as in (2) of Experiment 35 to obtain the entitled end product. Yield, 21.2 mg (27.9%).

Characteristics of the product: FAB-MS M+H: 2357 (Calcd. 2357).

UV Absorption: λ(shoulder), 287 nm; λmax 280 nm.

EXPERIMENT 41

Preparation of H—(1-18)—NH($CH_2$)$_3$$CH_3$.8HCl

Condensation was carried out in the same manner as in (1) of Experiment 35 except that $CH_3(CH_2)_3NH_2$ (3.9 mg, 53.9 μmol) was used in place of $CH_3(CH_2)_{11}NH_2$. Yield, 200 mg (98%).

A 100 mg portion of the product obtained in the above was unblocked and purified in the same manner as in (2) of Experiment 35 to obtain the entitled end product. Yield, 21.3 mg (28.6%).

Characteristics of the product: FAB-MS M+H: 2329 (Calcd. 2329).

UV Absorption: λ(shoulder), 287 nm; λmax 280 nm.

EXPERIMENT 42

Preparation of H—(1-18)—NH($CH_2$)$CH_3$.8HCl

Condensation was carried out in the same manner as in (1) of Experiment 35 except that $CH_3C(CH_2)NH_2$ (2.4 mg, 53.9 μmol) was used in place of $CH_3(CH_2)_{11}NH_2$. Yield, 199 mg (98.5%).

A 80 mg portion of the product obtained in the above was unblocked and purified in the same manner as in (2) of Experiment 35 to obtain the entitled end product. Yield, 17.1 mg (29.2%).

Characteristics of the product: FAB-MS M+H: 2301 (Calcd. 2301).

UV Absorption: λ(shoulder), 287 nm; λmax 280 nm.

III. ANTIBACTERIAL ACTIVITIES OF ANTIBACTERIAL SUBSTANCES OF THE INVENTION (EXAMPLES 1 TO 3)

EXAMPLE 1

Using the substances finally obtained in the above-described Experiments 35 to 42 and having no blocking group, MIC (minimum growth inhibitory concentration) against various bacteria was examined according to the broth dilution method, and the antibacterial activities were evaluated. Results are shown in Table 1.

TABLE 1

| Sample substance (1) | MIC (mcg/ml) (2) Bacteria (3) | | | | | | | | | | | | | |
|---|---|---|---|---|---|---|---|---|---|---|---|---|---|---|
| | P. mira 129 | P. mira 1287 | E. coli NIHJ | E. coli JC-2 | S. ent 3313 | P. aeru | P. aeru 99 | E. aero 13534 | S. aure 209-P | B. sub 219 | S. hemo | P. aeru OT 97 | E. coli D 21 | M. lute ML II |
| Synthetic lepidopteran A | 32 | 32 | 4 | 4 | 4 | 8 | 8 | 8 | 8 | 32 | — | 8 | 2 | 2 |
| H-(1-18)-NHC$_{18}$ | — | — | — | — | — | — | — | — | — | — | — | — | — | — |
| H-(1-18)-NHC$_{16}$ | — | — | 125 | 64 | 125 | 250 | 64 | — | 64 | 32 | — | 125 | 64 | 4 |
| H-(1-18)-NHC$_{14}$ | — | — | 32 | 32 | 32 | 64 | 32 | 125 | 32 | 8 | — | 32 | 32 | 4 |
| H-(1-18)-NHC$_{12}$ | — | — | 16 | 8 | 8 | 16 | 8 | 16 | 8 | 2 | — | 16 | 8 | 2 |
| H-(1-18)-NHC$_{10}$ | — | — | 8 | 4 | 4 | 4 | 8 | 8 | 8 | 2 | — | 8 | 4 | 2 |
| H-(1-18)-NHC$_{8}$ | 64 | 64 | 4 | 2 | 2 | 4 | 2 | 4 | 4 | 2 | — | 4 | 2 | 2 |
| H-(1-18)-NHC$_{6}$ | 32 | 32 | 4 | 4 | 4 | 64 | 8 | 16 | 8 | 8 | — | 8 | 4 | 2 |
| H-(1-18)-NHC$_{4}$ | 64 | 64 | 8 | 8 | 8 | 125 | 32 | 64 | 16 | 16 | — | 16 | 4 | 2 |
| H-(1-18)-NHC$_{2}$ | — | — | 16 | 16 | 8 | 250 | 64 | 125 | 16 | 32 | — | 64 | 4 | 2 |

Remarks:
(1) Sample substance: H-(1-18)-NH(CH$_2$)$_n$CH$_3$ is indicated as H-(1-18)-NHC$_{n+1}$
(2) Symbol "—" is meant to be MIC > 250 mcg/ml
(3) abbreviation for the name of bacteria:
P. mira 129: Proteus mirabilis 129
P. mira 1287: Proteus mirabilis 1287
E. coli NIHJ: Escherichia coli NIHJ
S. ent 3313: Salmonella enteritidis IFO 3313
P. aeru: Pseudomonas aeruginosa
P. aeru 99: Pseudomonas aeruginosa 99
E. aero 13534: Enterobacter aerogenes IFO 13545
S. aure 209P: Staphylococcus aureus FDA 209P
B. sub 219: Bacillus subtilis PCI 219
S. hemo: Streptococcus hemolyticus
P. aeru OT 97: Pseudomonas aeruginosa OT 97
E. coli D 21L Escherichia coli D 21
M. lute ML II: Micrococcus luteus ML II As will be seen from Table 1, there is shown little antibacterial activity when n≧17. High antibacterial activities can be shown against the particular bacteria, e.g., S. aure. 209-P or B. sub 219 when n=13. When n=11, good antibacterial activities can be obtained against S. aure. 209-P and B. sub 219. When n=3 to 9, there are shown antibacterial activities equal to or better than lepidopteran A. Very good antibacterial activities can be had particularly when n=7.

EXAMPLE 2

H—(1-23)—NH(CH$_2$)$_7$CH$_3$ was synthesized according to the same procedures as described in Experiments 1 to 35, and the antibacterial activities thereof against various bacteria were examined in the same manner as in Example 1.

Results obtained are shown in Table 2. For comparison, there are shown the results of evaluation on H—(1-18)—NH(CH$_2$)$_7$CH$_3$ and the synthetic lepidopteran A.

TABLE 2

| Sample substance | MIC (mcg/ml) (1) Bacteria | | | | | | | | | | | | | |
|---|---|---|---|---|---|---|---|---|---|---|---|---|---|---|
| | P. mira 129 | P. mira 1287 | E. coli NIHJ | E. coli JC-2 | S. ent 3313 | P. aeru | P. aeru 99 | E. aero 13534 | S. aure 209-P | B. sub 219 | S. hemo | P. aeru OT 97 | E. coli D 21 | M. lute ML II |
| H-(1-18)NH(CH$_2$)$_7$CH$_3$ | 64 | 64 | 4 | 2 | 2 | 4 | 2 | 4 | 4 | 2 | — | 4 | 2 | 2 |
| H-(1-23)NH(CH$_2$)$_7$CH$_3$ | 16 | 16 | 2 | 2 | 2 | 2 | 2 | 2 | 2 | 2 | — | 4 | 2 | 2 |
| Synthetic lepidopteran A | 32 | 32 | 4 | 4 | 4 | 8 | 8 | 8 | 125 | 32 | — | 8 | 2 | 2 |

Remarks:
(1) Symbol "—" is meant to be MIC > 250 mcg/ml

Reviewing Table 2, it is seen that H—(1-23)—NH(CH$_2$)$_7$CH$_3$ has better antibacterial activities than H—(1-18)—NH(CH$_2$)$_7$CH$_3$ and the synthetic lepidopteran A in respect of all bacterial.

EXAMPLE 3

The number of amino acid residues of the resulting H—(1-18)—NH—R (wherein R is (—(CH$_2$)$_n$CH$_3$) was analyzed with use of an amino acid analyzer (produced by Hitachi, Ltd.) to obtain the results as shown in Table 3 (wherein R is expressed by the carbon atom number contained therein).

TABLE 3

| R: | H-(1-18)-NH-R | | | |
|---|---|---|---|---|
| | C$_{18}$ | C$_{16}$ | C$_{14}$ | C$_{12}$ |
| Asp (2)** | 1.97 | 1.85 | 1.95 | 1.82 |
| Glu (1) | 1.05 | 1.00 | 1.16 | 1.04 |
| Gly (2) | 1.93 | 1.96 | 1.99 | 1.98 |
| Met (1) | 1.00 | 1.05 | 1.17 | 1.11 |
| Ile (3) | 2.96 | 2.92 | 3.15 | 2.77 |
| Phe (1) | 1.00 | 1.04 | 1.00 | 1.00 |
| Lys (4) | 4.32 | 4.33 | 4.52 | 3.96 |
| Trp (1)* | 0.59 | 0.81 | 1.02 | 0.92 |
| Arg (3) | 2.94 | 3.46 | 3.06 | 3.40 |

Remarks:
6M-HCl. 110° C., 90 h.
*24 h.
**Theoretical residue number is shown in ( ).

It is seen from the results shown in Table 3 that those substantially R contains 12 to 18 carbon atoms are substantially coincident with the theoretical residue number. Accordingly, each of them can be considered to have been substantially perfectly synthesized.

What is claimed is:

1. An antibacterial peptide having from 18 to 23 amino acid residues and having the same amino acid sequence as Lepidopteran A, beginning with the N-terminal arginine and ending with amino acid 18-23 of the Lepidopteran A sequence, wherein the carboxyl group at the C-terminus of said peptide is converted to the octylamide group having the formula —CONH(CH$_2$)$_7$CH$_3$.

* * * * *